US012295779B2

United States Patent
Taya et al.

(10) Patent No.: US 12,295,779 B2
(45) Date of Patent: May 13, 2025

(54) RADIATION IMAGING SYSTEM AND CONTROL METHOD THEREOF

(71) Applicant: CANON KABUSHIKI KAISHA, Tokyo (JP)

(72) Inventors: Takanori Taya, Kanagawa (JP); Toshikazu Tamura, Tochigi (JP); Sota Torii, Tokyo (JP); Tetsunori Ojima, Kanagawa (JP); Kentaro Fujiyoshi, Irvine, CA (US)

(73) Assignee: CANON KABUSHIKI KAISHA, Tokyo (JP)

( * ) Notice: Subject to any disclaimer, the term of this patent is extended or adjusted under 35 U.S.C. 154(b) by 234 days.

(21) Appl. No.: 17/894,231

(22) Filed: Aug. 24, 2022

(65) Prior Publication Data
US 2022/0401054 A1 Dec. 22, 2022

Related U.S. Application Data

(63) Continuation of application No. PCT/JP2021/007706, filed on Mar. 1, 2021.

(30) Foreign Application Priority Data

Mar. 4, 2020 (JP) ................. 2020-036784
Mar. 4, 2020 (JP) ................. 2020-036975

(51) Int. Cl.
*A61B 6/00* (2024.01)
*A61B 6/10* (2006.01)
*A61B 6/40* (2024.01)
*A61B 6/42* (2024.01)

(52) U.S. Cl.
CPC .............. *A61B 6/542* (2013.01); *A61B 6/107* (2013.01); *A61B 6/4035* (2013.01); *A61B 6/42* (2013.01)

(58) Field of Classification Search
CPC ....... A61B 6/542; A61B 6/107; A61B 6/4035; A61B 6/42
See application file for complete search history.

(56) References Cited

U.S. PATENT DOCUMENTS

| 4,639,943 A | 1/1987 | Heinze et al. |
| 9,232,620 B2 | 1/2016 | Tajima |
| 9,301,725 B2 | 4/2016 | Kaneko et al. |

(Continued)

FOREIGN PATENT DOCUMENTS

| EP | 2601891 A1 | 6/2013 |
| JP | 60140399 U | 9/1985 |

(Continued)

*Primary Examiner* — Dani Fox
*Assistant Examiner* — Casey Bryant
(74) *Attorney, Agent, or Firm* — VENABLE LLP

(57) ABSTRACT

A radiation imaging system comprises a sensor unit of a radiation imaging device, detecting an incident radiation R irradiated from a radiation generator; an arithmetic unit calculating an accumulated dose of the radiation detected by the sensor unit; and an imaging control unit outputting an irradiation stop signal for stopping the irradiation of the radiation R to the radiation generator when the accumulated dose reaches a threshold or more, wherein the imaging control unit sets the threshold based on a dose rate of the radiation R determined based on a relationship between the accumulated dose and a time, and a delay time from a time of outputting the irradiation stop signal to a time of stopping the irradiation of the radiation of the radiation generator.

20 Claims, 7 Drawing Sheets

(56) References Cited

U.S. PATENT DOCUMENTS

| | | |
|---|---|---|
| 2013/0121464 A1 | 5/2013 | Tajima |
| 2013/0148784 A1 | 6/2013 | Tajima |
| 2014/0119509 A1 | 5/2014 | Kaneko et al. |
| 2016/0038114 A1 | 2/2016 | Tajima |

FOREIGN PATENT DOCUMENTS

| | | |
|---|---|---|
| JP | 2013-138829 A | 7/2013 |
| JP | 2014-87513 A | 5/2014 |
| JP | 2017-209244 | 11/2017 |
| JP | 2021-137271 A | 9/2021 |
| WO | 2017/006543 A1 | 1/2017 |

RADIATION IMAGING SYSTEM AND CONTROL METHOD THEREOF

CROSS-REFERENCE TO RELATED APPLICATIONS

This application is a Continuation of International Patent Application No. PCT/JP2021/007706, filed Mar. 1, 2021, which claims the benefit of Japanese Patent Application No. 2020-036784, filed Mar. 4, 2020, and Japanese Patent Application No. 2020-036975, filed Mar. 4, 2020, all of which are hereby incorporated by reference herein in their entirety.

BACKGROUND OF THE INVENTION

Field of the Invention

A disclosure of a present specification relates to a radiation imaging system for performing a radiation imaging and a method for controlling the same.

Description of the Related Art

At present, radiation imaging apparatuses equipped with a flat panel detector (FPD) formed of a semiconductor material are widely used as radiation imaging apparatuses used for medical imaging diagnosis and nondestructive examination using radiation such as X-ray. Such a radiation imaging apparatus is used, for example, as a digital radiation imaging apparatus for taking still images such as general photographing and for taking moving images such as fluoroscopy in medical image diagnosis.

Some radiation imaging apparatuses monitor the dose of irradiated radiation (accumulated dose) and stop the irradiation of the radiation when the accumulated dose reaches a threshold (for example, an irradiation stop signal for stopping the irradiation of the radiation is output to a radiation generator.). This operation is called Automatic Exposure Control (AEC), which can prevent, for example, excessive irradiation of the radiation.

As such a radiation imaging apparatus, for example, Japanese Patent Application Laid-Open No. 2013-138829 discloses a radiation imaging apparatus including a dose detection unit for detecting a dose of the radiation reaching an imaging area, in the imaging area of the FPD. In this Japanese Patent Application Laid-Open No. 2013-138829 the stopping timing at which the irradiation of the radiation should be stopped in the radiation generator is predicted based on the dose detected by the dose detection unit and a dose target value set in advance, and the irradiation stopping timing notification for informing the radiation generator of the irradiation stopping timing of the radiation is transmitted before the irradiation stopping timing arrives.

However, the technique disclosed in Japanese Patent Application Laid-Open No. 2013-138829 has a problem in the accuracy of an irradiation stop control of the radiation from the radiation generator. In other words, in the technique described in Japanese Patent Application Laid-Open No. 2013-138829, when the transmitted dose rate of the radiation that passes through the object becomes high, the time required for the accumulated dose of the radiation to reach the threshold is shortened to about several ms (milliseconds), and as a result, the accumulated dose of the radiation becomes larger than the threshold before the radiation generator stops the irradiation due to the delay in the notification of the irradiation stop timing.

SUMMARY OF THE INVENTION

In consideration of the above-described matters, it is an object of the present disclosure to provide a mechanism capable of controlling the irradiation stop of the radiation from the radiation generator with high accuracy.

A radiation imaging apparatus disclosed herein comprises: a sensor unit configured to detect an incident radiation irradiated from a radiation generator; an arithmetic unit configured to calculate an accumulated dose of the radiation detected by the sensor unit; and a control unit configured to output an irradiation stop signal for stopping the irradiation of the radiation to the radiation generator when the accumulated dose reaches a threshold or more, wherein the control unit sets the threshold based on a dose rate of the radiation determined based on a relationship between the accumulated dose and a time, and a delay time from a time of outputting the irradiation stop signal to a time of stopping the irradiation of the radiation of the radiation generator.

The disclosure also includes methods for controlling the radiation imaging system described above.

The purpose of the disclosure of the present specification is not limited to one of the above-described purposes. One of the other purposes of the present invention is to provide working effects derived from the respective configurations shown in the embodiments to be described later as an embodiment for carrying out the disclosure, which cannot be obtained by the prior art.

Further features of the present invention will become apparent from the following description of exemplary embodiments with reference to the attached drawings.

DESCRIPTION OF THE EMBODIMENTS

Hereinafter, the embodiments disclosed herein will be described with reference to the drawings. In the present specification, it is preferable to use X-rays as the radiation, but the radiation is not limited to the X-ray, and it is assumed that a-rays, (3-rays, y-rays and the like are also included in the radiation to be used.

First Embodiment

Firstly, a first embodiment will be described.

Figure 1:
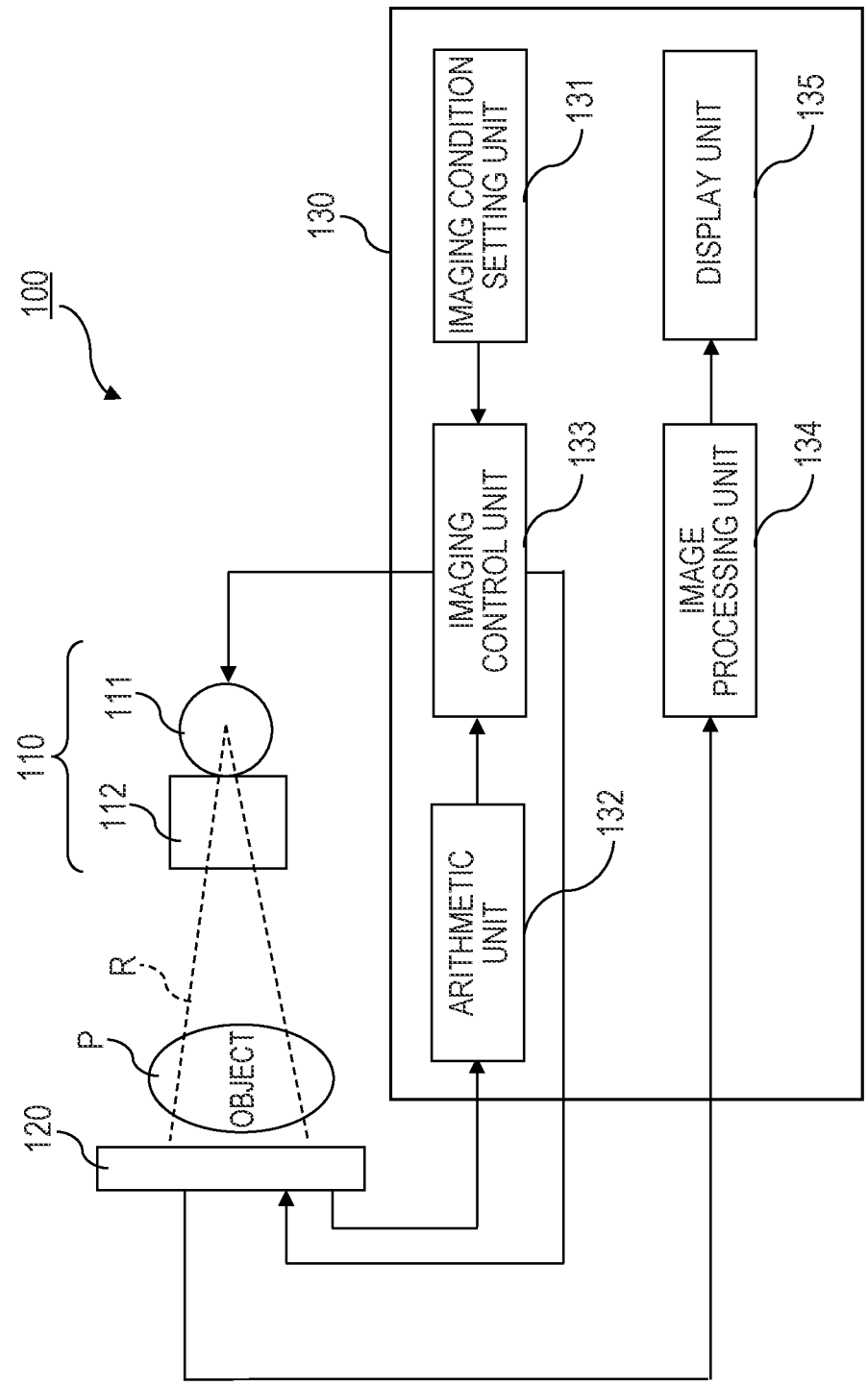
FIG. 1 is a diagram showing an example of a schematic configuration of a radiation imaging system according to a first embodiment

FIG. 1 is a diagram showing an example of a schematic configuration of a radiation imaging system 100 according to a first embodiment. In this embodiment, the radiation imaging system 100 is particularly suitable for medical use. As shown in FIG. 1, the radiation imaging system 100 is configured by including a radiation generator 110, a radiation imaging device 120, and a control unit 130. The control unit 130 is configured to be capable of communicating with the radiation generator 110 and the radiation imaging device 120, and includes an imaging condition setting unit 131, an arithmetic unit 132, an imaging control unit 133, an image processing unit 134, and a display unit 135.

The radiation generator 110 irradiates the object P with the radiation R under a control of the control unit 130 (more specifically, the imaging control unit 133.). The radiation generator 110 includes a radiation tube 111 which is a radiation generator unit for generating the radiation R, and a collimator 112 which defines a beam spreading angle of the radiation R generated by the radiation tube 111.

The radiation imaging device 120 includes, for example, an FPD, and includes a sensor unit including an imaging element distributed in two dimensions. The sensor unit detects the incident radiation R irradiated from the radiation generator 110. The radiation imaging device 120 specifically detects information (dose information) on the two-dimensional distribution of the radiation dose that has reached the imaging elements in the sensor unit, and generates radiation image data. Thereafter, the radiation imaging device 120 transmits the generated radiation image data to the image processing unit 134 of the control unit 130. The radiation imaging device 120 transmits information (dose information) on the two-dimensional distribution of the radiation dose detected by the sensor unit to the arithmetic unit 132 of the control unit 130.

The control unit 130 controls operations of the radiation generator 110 and the radiation imaging device 120, and acquires and processes dose information detected by the sensor unit of the radiation imaging device 120 and radiation image data imaged by the radiation imaging device 120.

Next, the functions of the respective components 131-135 provided in the control unit 130 will be described. The imaging condition setting unit 131 sets imaging condition data including, for example, imaging condition information such as an imaging region of the object P, the tube voltage and tube current in the radiation tube 111, a delay time, a reference value Dref of the dose (accumulated dose) at which the radiation R passes through the object P and reaches the radiation imaging device 120, and a threshold Dth for controlling an output of the irradiation stop signal to the radiation generator 110, which are input by an operator. Then, the imaging condition setting unit 131 transmits necessary imaging condition information among the set imaging condition data to the imaging control unit 133. Here, the dose generally means the accumulated dose achieved at the time of an irradiation of the radiation, but a dose value similar thereto may be used, and the term of "accumulated dose" will be used in the following, if necessary.

The arithmetic unit 132 calculates the accumulated dose of the radiation R detected by the sensor unit of the radiation imaging device 120 based on the dose information transmitted from the radiation imaging device 120, and transmits the calculated accumulated dose to the imaging control unit 133.

The imaging control unit 133 controls the radiation generator 110 and the radiation imaging device 120 based on the imaging condition information received from the imaging condition setting unit 131 and information of the accumulated dose received from the arithmetic unit 132.

The image processing unit 134 performs image processing such as gradation processing and noise reduction processing on the radiation image data transmitted from the radiation imaging device 120. Then, the image processing unit 134 transmits the radiation image data after the image processing to the display unit 135.

The display unit 135 outputs a radiation image based on the radiation image data transmitted from the image processing unit 134 to a monitor or the like to display it.

The delay time set by the imaging condition setting unit 131 is a time period from a time when an irradiation stop signal for stopping the irradiation of the radiation R is outputted from the imaging control unit 133 to the radiation generator 110 based on the accumulated dose of the radiation R calculated by the arithmetic unit 132 to a time when the irradiation of the radiation R is stopped in the radiation generator 110. The time at which the irradiation of the radiation R is stopped in the radiation generator 110 is a time at which the tube voltage in the radiation tube 111 of the radiation generator 110 starts to decrease or a time at which the tube voltage completely decreases. In a case where the delay time is set based on the time when the tube voltage in the radiation tube 111 of the radiation generator 110 completely falls, it is desirable to set the delay time by considering the time obtained by multiplying the time of the unsteady period from the time when the tube voltage in the radiation tube 111 starts to fall to the time when the tube voltage in the radiation tube completely falls by a coefficient considering the change in dose and radiation quality.

Firstly, a process of the pre-imaging to be performed prior to the irradiation of the radiation R for the main-imaging of the object P will be described with reference to FIGS. 2 and 3.

Figure 2:
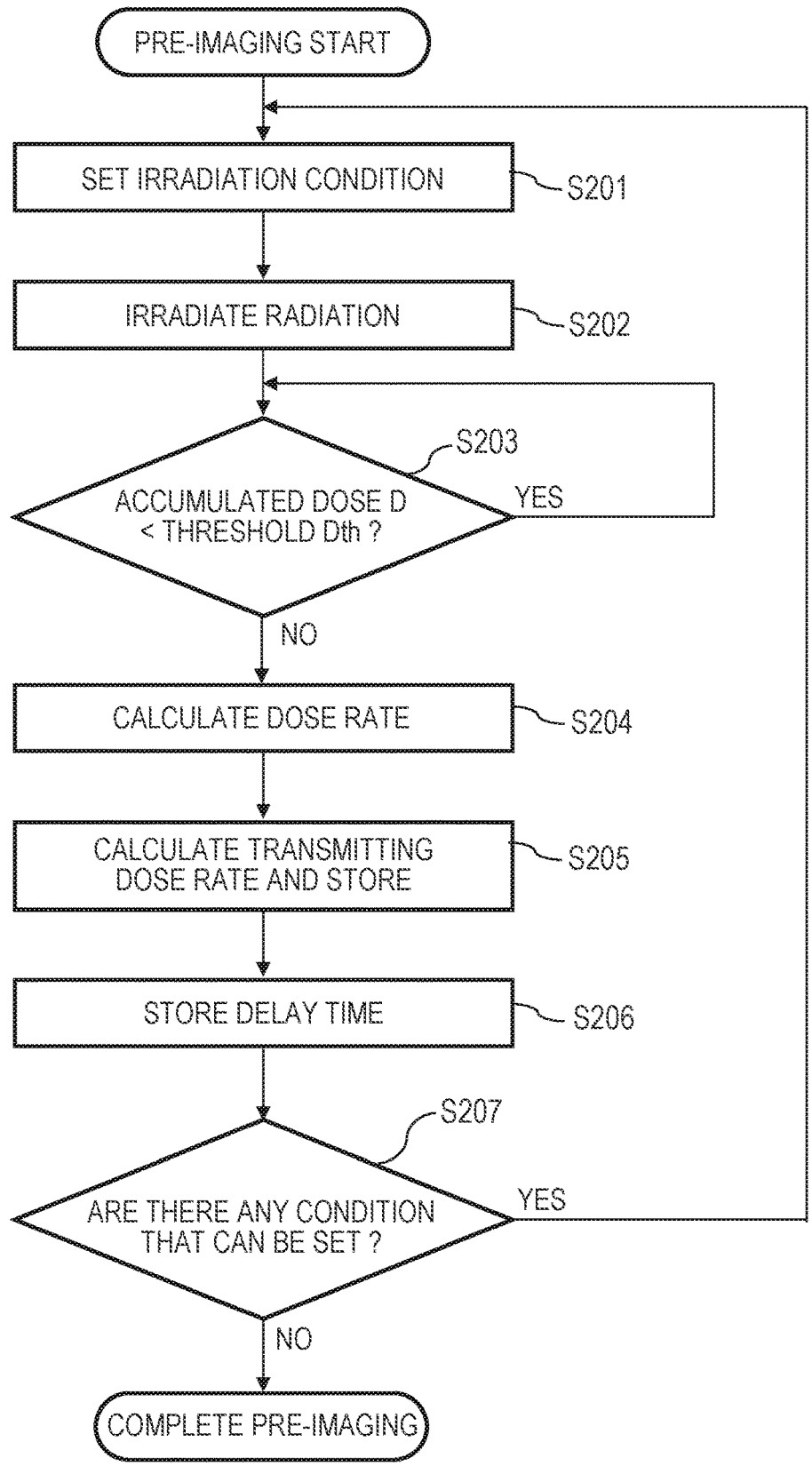
FIG. 2 is a flowchart showing an example of a processing procedure in a series of control methods from a start to an end of a pre-imaging performed before an irradiation of a radiation relating to a main-imaging of an object in the radiation imaging system according to the first embodiment.

FIG. 2 is a flowchart showing an example of a processing procedure in a series of control methods from a start to an end of pre-imaging performed before the irradiation of the radiation R for the main-imaging of the object P in the radiation imaging system 100 according to the first embodiment disclosed herein. FIG. 3 is a diagram for explaining the series of control methods from the start to the end of pre-imaging of the object P before the irradiation of the radiation R for the main-imaging in the radiation imaging system 100 according to the first embodiment disclosed herein. FIG. 3 shows the relationship between the accumulated dose D (vertical axis) and time (horizontal axis).

Figure 3:
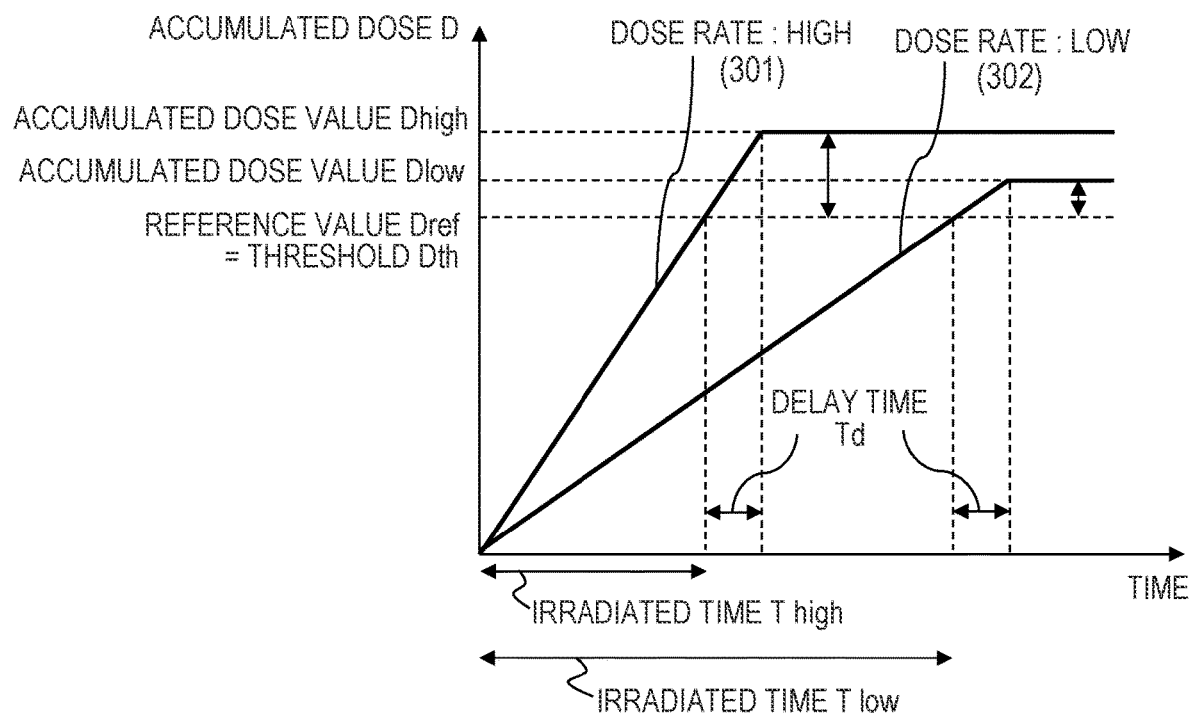
FIG. 3 is a diagram for explaining the series of control methods from the start to the end of the pre-imaging performed before the irradiation of the radiation relating to the main-imaging of the object in the radiation imaging system according to the first embodiment.

In the pre-imaging process shown in FIG. 2, the transmitted dose rate of the radiation R which passes through the object P and reaches the radiation imaging device 120 is estimated to at least one of the tube voltage and the tube current in the radiation tube 111 set in each pre-imaging (in this embodiment, for example, each of the tube voltages and each of the tube currents are assumed.), and the estimated dose rate is stored in a database for use in setting a threshold at the time of main-imaging together with a delay time Td shown in FIG. 3.

Firstly, in step S201, the imaging condition setting unit 131 receives an instruction to start a pre-imaging inputted by an operator via an input unit (not shown), and sets imaging condition information (irradiation condition information) inputted by the operator, for example. Here, the imaging condition setting unit 131 sets, as the imaging condition information (irradiation condition information), a tube voltage and a tube current in the radiation tube 111, a reference value Dref of the accumulated dose, a threshold Dth, and the like. Here, the imaging condition setting unit 131 sets the threshold Dth equal to the reference value Dref of the accumulated dose, as shown in FIG. 3. Thereafter, the imaging condition setting unit 131 transmits the acquired instruction for starting the pre-imaging and the set imaging condition information (irradiation condition information) to the imaging control unit 133.

Next, in step S202, the imaging control unit 133 transmits an irradiation execution signal for irradiating the radiation R to the radiation generator 110 together with the imaging condition information (irradiation condition information) received from the imaging condition setting unit 131 in step S201. Accordingly, the radiation generator 110 irradiates the radiation R toward the radiation imaging device 120 under the irradiation conditions based on the imaging condition information (irradiation condition information) set in step S201.

Subsequently, in step S203, the arithmetic unit 132 calculates a value D representing the accumulated dose of the radiation R detected by the sensor unit based on the dose information (for example, dose information for each imaging element in the sensor unit) transmitted from the radiation imaging device 120. The value D representing the accumulated dose of the radiation R may be a maximum value, an average value, a median value or the like of the accumulated dose. In the following description, the value D representing the accumulated dose of the radiation R is described as "accumulated dose D of the radiation R". The arithmetic unit 132 transmits the calculated accumulated dose D of the radiation R to the imaging control unit 133. Next, the imaging control unit 133 compares the accumulated dose D of the radiation R received from the arithmetic unit 132 with the threshold Dth set in step S201, and determines whether or not the accumulated dose D is smaller than the threshold Dth. As a result of this determination, if the accumulated dose D is smaller than the threshold Dth (step S203/YES), the process waits in step S203.

On the other hand, if it is determined in step S203 that the accumulated dose D is not smaller than the threshold Dth (that is, the accumulated dose D is equal to or larger than the threshold) (step S203/NO), the process proceeds to step S204. In step S204, the imaging control unit 133 calculates a dose rate of the radiation R to be irradiated to the radiation imaging device 120 based on the accumulated dose D of the radiation R received from the arithmetic unit 132 in step S203 and the irradiation time of the radiation R. In the example shown in FIG. 3, when the dose rate of the radiation R incident on the radiation imaging device 120 is high, the dose rate 301 can be calculated from the reference value Dref (=threshold Dth) of the accumulated dose and the irradiation time Thigh. When the dose rate of the radiation R incident on the radiation imaging device 120 is low, the dose rate 302 can be calculated from the reference value Dref (=threshold Dth) of the accumulated dose and the irradiation time Tlow. As shown in FIG. 3, the dose rate 301 and the dose rate 302 of the radiation R are determined based on the relationship between the accumulated dose D and time.

Subsequently, in step S205, the imaging control unit 133 estimates a transmitted dose rate of the radiation R based on the dose rate of the radiation R acquired in step S204 and the transmission rate assumed for the object P. Here, the transmission rate assumed for the object P may be obtained based on a radiation shield information such as filter condition information relating to a filter simulating a human body at the time of the irradiation of the radiation R in step S202 and object information including the transmittance of a general human body. As the transmittance assumed for the object P, the transmittance of a general human body may be calculated by referring to the imaging data in the past. The transmitted dose rate of the radiation R estimated in step S205 is stored in the database in correspondence with the tube voltage and tube current in the radiation tube 111, which is the imaging condition information, and the filter condition information and/or the object information.

Subsequently, in step S206, the imaging control unit 133 obtains the delay time Td shown in FIG. 3. In the example shown in FIG. 3, when the dose rate of the radiation R incident on the radiation imaging device 120 is high, the delay time Td can be calculated using the accumulated dose value Dhigh, and the stored dose rate 301 (in addition, using the reference value of the accumulated dose Dref (=threshold Dth)). When the dose rate of the radiation R incident on the radiation imaging device 120 is low, the delay time Td can be calculated using the accumulated dose value Dlow, and the stored dose rate 302 (in addition, using the reference value of the accumulated dose Dref (=threshold Dth)). Although an example of calculating the delay time Td has been described here, the delay time Td may be actually measured and obtained. The delay time Td obtained in step S206 is stored in the database in the same manner as the transmitted dose rate of the radiation R calculated and stored in step S205.

Subsequently, in step S207, the imaging control unit 133 determines whether or not a settable imaging condition (irradiation condition) still exists. As a result of this determination, if there is still a settable imaging condition (irradiation condition) (step S207/YES), the process returns to step S201, and the processing after step S201 are performed for the settable imaging condition (irradiation condition).

On the other hand, if there is no settable imaging condition (irradiation condition) as a result of the determination in step S207 (step S207/NO), the process of the flowchart relating to the pre-imaging shown in FIG. 2 is ended.

By the above processing, the transmitted dose rate and the delay time Td of the radiation R can be calculated for each of the imaging condition information such as the tube voltage and the tube current in the radiation tube 111 and for each of the radiation shield information such as the filter condition information and the object information.

Next, the main-imaging process of the object P will be described with reference to FIGS. 4 and 5.

Figure 4:
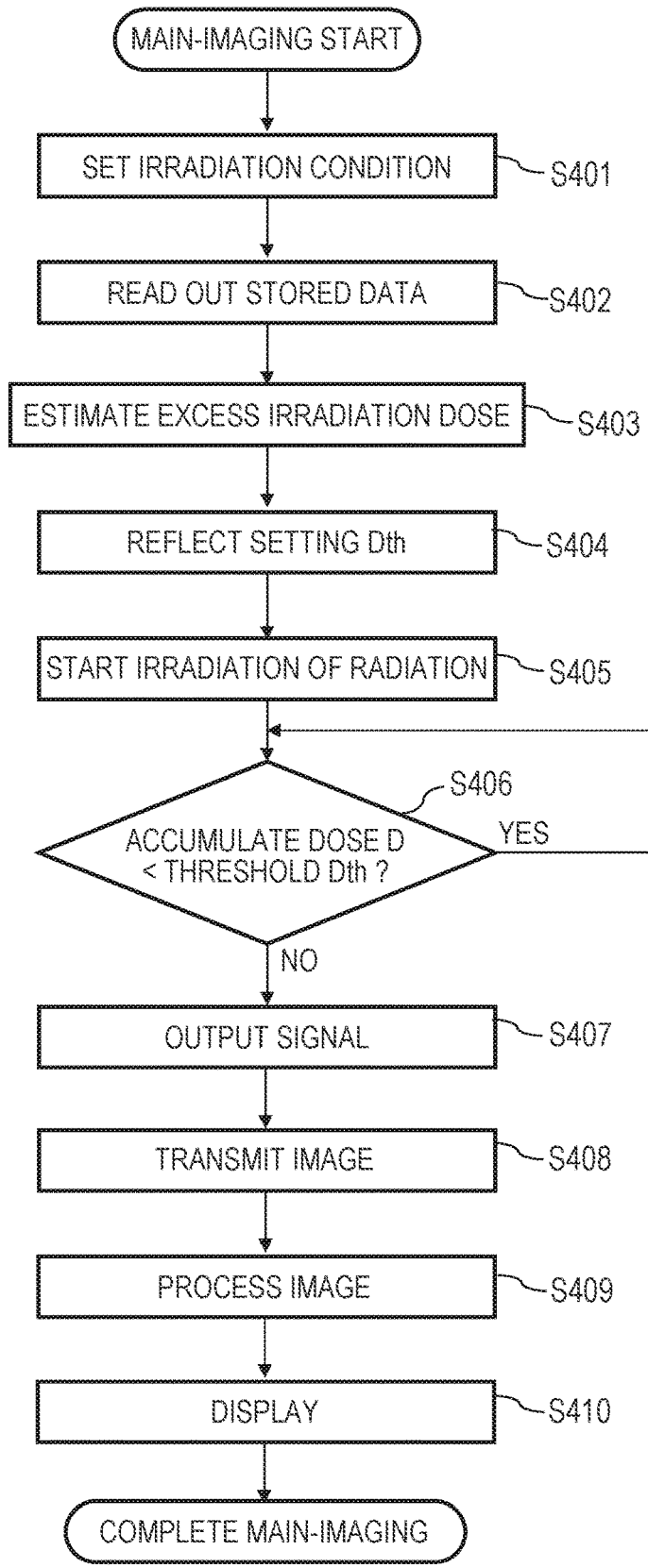
FIG. 4 is a flowchart showing an example of a processing procedure in a series of control methods from a start to an end of the main-imaging of the object in the radiation imaging system according to the first embodiment.

FIG. 4 is a flowchart showing an example of a processing procedure in a series of control methods from a start to an end of main-imaging of the object P in the radiation imaging system 100 according to the first embodiment. FIG. 5 is a diagram for explaining the series of control methods from the start to the end of main-imaging of the object P in the radiation imaging system 100 according to the first embodiment. FIG. 5 shows the relationship between accumulated dose D (vertical axis) and time (horizontal axis).

In the main-imaging process, the irradiation dose (FIG. 5) due to the delay time Td is estimated using various information acquired in the prior pre-imaging process described with reference to FIGS. 2 and 3, and reflected in the setting of the threshold Dth shown in FIG. 5 to perform the radiation imaging of the object P.

Firstly, in step S401, the imaging condition setting unit 131 receives an instruction to start the main-imaging inputted by the operator via the input unit (not shown), and sets imaging condition information (irradiation condition information) inputted by the operator, for example. Here, the imaging condition setting unit 131 sets, as imaging condition information (irradiation condition information), a tube voltage and a tube current in the radiation tube 111, a reference value Dref of the accumulated dose, and the like. Thereafter, the imaging condition setting unit 131 transmits the acquired instruction for starting the main-imaging and the set imaging condition information (irradiation condition information) to the imaging control unit 133.

Subsequently, in step S402, the imaging control unit 133 reads the transmitted dose rate and the delay time Td of the radiation R stored in the pre-imaging process described with reference to FIGS. 2 and 3 based on the imaging condition information (irradiation condition information) acquired in step S401. That is, here, the transmitted dose rate and the delay time Td of the radiation R stored before the irradiation of the radiation R in step S405, which will be described later, are read out.

Subsequently, in step S403, the imaging control unit 133 multiplies the transmitted dose rate of the radiation R read in step S402 by the delay time Td read in step S402 to estimate the irradiation dose (excess irradiation dose) due to the delay time Td shown in FIG. 5.

Subsequently, in step S404, the imaging control unit 133 sets the threshold Dth shown in FIG. 5 based on the irradiation dose due to the delay time Td estimated in step S403 and the reference value Dref of the accumulated dose D. Specifically, in step S404, the imaging control unit 133 sets a value obtained by subtracting the irradiation dose in the delay time Td estimated in step S403 from the reference value Dref of the accumulated dose D, as the threshold Dth. As described above, in step S404, the threshold Dth is set by correcting the reference value Dref of the accumulated dose D.

Subsequently, in step S405, the imaging control unit 133 transmits an irradiation execution signal for irradiating the radiation R to the radiation generator 110 together with the imaging condition information (irradiation condition information) received from the imaging condition setting unit 131 in step S401. Accordingly, the radiation generator 110 irradiates the object P with radiation R under the irradiation conditions based on the imaging condition information (irradiation condition information) received from the imaging condition setting unit 131 and the threshold Dth set in step S404.

Subsequently, in step S406, the arithmetic unit 132 calculates a value D representing the accumulated dose of the radiation R detected by the sensor unit based on the dose information (for example, dose information for each of the imaging elements in the sensor unit) transmitted from the radiation imaging device 120. The value D representing the accumulated dose of the radiation R may be a maximum value, an average value, a median value or the like of the accumulated dose. In the following description, the value D representing the accumulated dose of the radiation R is described as "accumulated dose D of the radiation R". Then, the imaging control unit 133 compares the accumulated dose D of the radiation R received from the arithmetic unit 132 with the threshold Dth set in step S404, and determines whether or not the accumulated dose D is smaller than the threshold Dth. As a result of this determination, if the accumulated dose D is smaller than the threshold Dth (step S406/YES), the process waits in step S406.

On the other hand, if it is determined in step S406 that the accumulated dose D is not smaller than the threshold Dth (that is, the accumulated dose D is equal to or larger than the threshold) (step S406/NO), the process proceeds to step S407. In step S407, since the accumulated dose D has exceeded (reached) the threshold Dth, the imaging control unit 133 outputs the irradiation stop signal for stopping the irradiation of the radiation R to the radiation generator 110. At this time, since the radiation R is continuously irradiated in a period of the delay time Td from the output of the irradiation stop signal from the imaging control unit 133 to the radiation generator 110 until the irradiation of the radiation R is actually stopped in the radiation generator 110, the accumulated dose D actually irradiated can be made close to the reference value Dref of the accumulated dose D.

Subsequently, in step S408, the imaging control unit 133 firstly transmits an imaging control signal to the radiation imaging device 120. The radiation imaging device 120 controls the imaging elements in the sensor unit based on the imaging control signal received from the imaging control unit 133, stops a conversion to the dose information after a predetermined time has elapsed from a reception of the imaging control signal, and transmits the generated radiation image data to the image processing unit 134.

Subsequently, in step S409, the image processing unit 134 performs the image processing such as a gradation processing and a noise reduction processing on the radiation image data received from the radiation imaging device 120. Thereafter, the image processing unit 134 transmits the radiation image data after the image processing to the display unit 135.

Subsequently, in step S410, the display unit 135 outputs a radiation image based on the radiation image data received from the image processing unit 134 to a monitor or the like for display, and presents the radiation image to the operator.

When the processing of step S410 is completed, the processing of the flowchart of the main-imaging shown in FIG. 4 is completed.

In the radiation imaging system 100 according to the first embodiment, the radiation imaging unit 133 outputs the irradiation stop signal to the radiation generator 110 when the accumulated dose D of the radiation R detected by the sensor unit of the radiation imaging device 120 becomes a threshold Dth or more. In this case, the imaging control unit 133 is configured to set the threshold Dth based on the dose rate of the radiation R determined based on the relationship between the accumulated dose D of the radiation R and the time, and the delay time Td from the output of the irradiation stop signal to the radiation generator 110 to the stop of the irradiation of the radiation R in the radiation generator 110. According to this configuration, since the threshold Dth is set in consideration of the dose rate and the delay time Td of the radiation R, the stop control of the irradiation of the radiation R from the radiation generator 110 can be performed with high accuracy. That is, the AEC can be performed with high accuracy.

Second Embodiment

Next, a second embodiment disclosed herein will be described. In the description of the second embodiment described below, matters common to those in the first embodiment described above will be omitted, and matters different from those in the first embodiment described above will be described.

Figure 5:
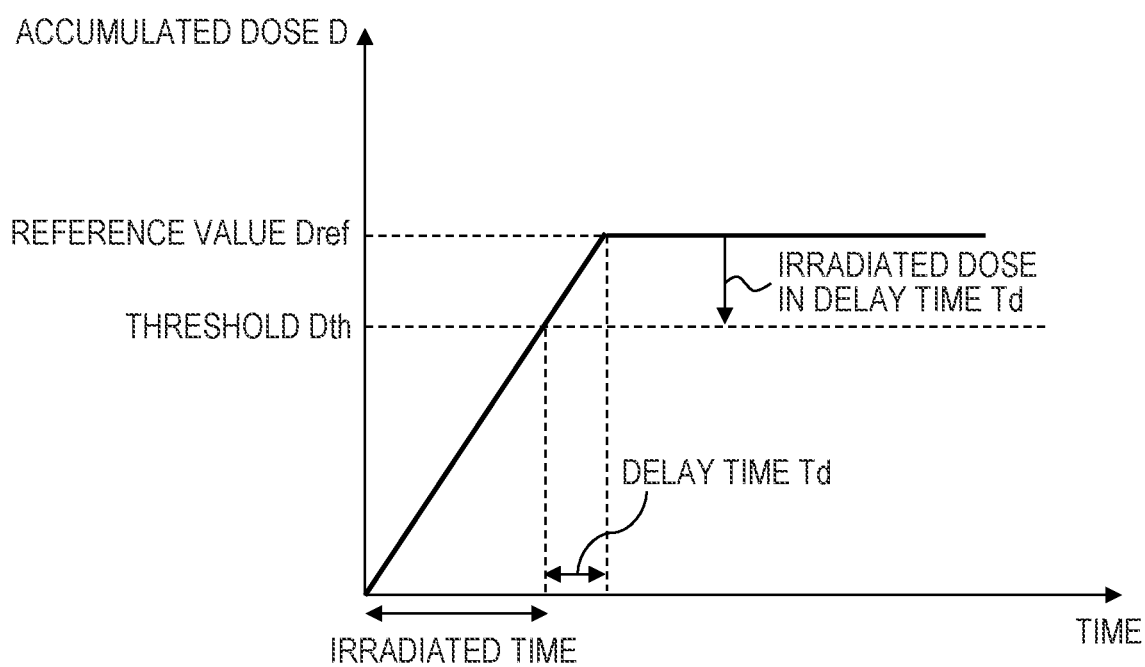
FIG. 5 is a diagram for explaining the series of control methods from the start to the end of main-imaging of the object in the radiation imaging system according to the first embodiment.

In the second embodiment, the difference from the first embodiment is that the information acquired or used in the main-imaging processing in FIGS. 4 and 5 is fed back and stored in the database as the imaging condition data, and the database used for the next and subsequent main-imaging processing is updated. In the second embodiment, the imaging condition data to be fed back and stored in the database includes at least the dose rate (transmitted dose rate) of the radiation R, the delay time Td, the amount of deviation between the reference value Dref of the accumulated dose D and the value of the actual accumulated dose D, and an object information.

In the first embodiment described above, the transmitted dose rate and the delay time Td of the radiation R are calculated or acquired at the time of processing of the pre-imaging, and stored in the database. On the other hand, in the second embodiment, as described above, object information and the like such as the amount of deviation between the reference value Dref of the accumulated dose D set at the time of the main-imaging processing and the actually obtained value of the accumulated dose D, the transmitted dose rate of the radiation R and the delay time Td, and the transmitted dose rate in consideration of the effect of the object thickness are added to or updated in the database. According to the configuration of the second embodiment, compared with the first embodiment, the accumulated dose D caused by the irradiation of the radiation R can be accurately approximated to the reference value Dref.

Specifically, in the second embodiment, after transmitting the image in step S408 of the main-imaging processing shown in FIG. 4, the amount of deviation between the reference value Dref of the accumulated dose D and the actual accumulated dose D is added to the database and stored. It is assumed that the amount of the deviation is caused by the difference in the transmitted dose rate of the radiation R estimated in the pre-imaging processing due to the effect of the object thickness or the like. In this case, when the deviation amount is a positive value, it is considered that the object thickness is thin and the transmitted dose rate of the radiation R is higher than estimated, and conversely, when the deviation amount is a negative value, it is considered that the object thickness is thick and the transmitted dose rate of the radiation R is lower than estimated. Therefore, in the second embodiment, the transmitted dose rate of the radiation R is re-estimated in consideration of the deviation amount, and is added to and updated in the database together with the object information. In the subsequent main-imaging processing, data to be read from the updated database is selected together with the object information when the stored data is read in step S402.

In the second embodiment, since the estimation accuracy of the transmitted dose rate of the radiation R can be improved by adding or updating the database by the above-described processing, the accumulated dose D caused by the irradiation of the radiation R can be accurately approximated to the reference value Dref.

Third Embodiment

Next, a third embodiment disclosed herein will be described. In the description of the third embodiment described below, matters common to those in the first embodiment and the second embodiment described above will be omitted, and matters different from those in the first embodiment and the second embodiment described above will be described.

The arithmetic unit 132 calculates the dose (accumulated dose) of the radiation R detected by the sensor unit of the radiation imaging device 120 based on the dose information transmitted from the radiation imaging device 120, and transmits the calculated dose to the imaging control unit 133.

The imaging control unit 133 controls the radiation generator 110 and the radiation imaging device 120 based on the imaging condition information received from the imaging condition setting unit 131 and the dose (accumulated dose) information received from the arithmetic unit 132. In the present embodiment, it is necessary to acquire the delay time Td for each of the imaging environments before irradiation (before imaging) of the radiation R relating to the radiation imaging of the object P. As the delay time Td, a value actually measured when the radiation imaging device 120 is installed can be used. Further, the imaging environment and the radiation generator 110 to be used may be registered in the database in advance, and the delay time Td may be calculated by referring to the database. The delay time Td is divided into a stationary period Ta from the signal transmission until the tube voltage starts to decrease and a non-stationary period Tb from the start of the tube voltage decrease until the tube voltage completely decreases. At this time, the non-stationary period Tb is added by multiplying the coefficient k (where the coefficient k is less than or equal to 1) because the tube voltage in the radiation tube 111 is lowered in the non-stationary period Tb. That is, the delay time Td when the non-stationary period Tb is considered can be determined based on the following equation.

$$Td=Ta+kTb$$

Next, a processing of imaging the object P will be described with reference to FIG. 6.

Figure 6:
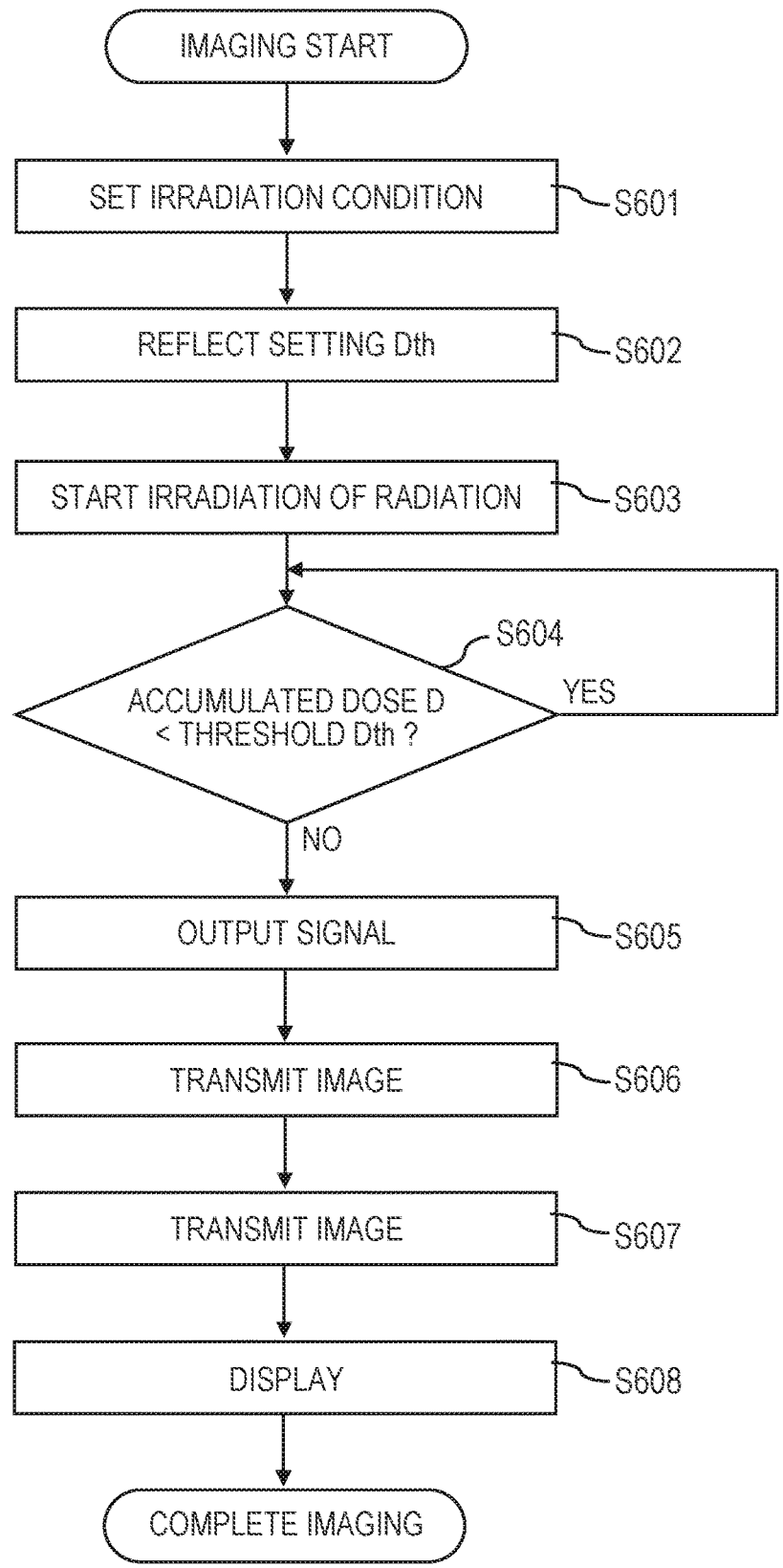
FIG. 6 is a flowchart showing an example of a processing procedure in a series of control methods from a start to an end of imaging an object in a radiation imaging system according to a third embodiment.

FIG. 6 is a flowchart showing an example of a processing procedure in a series of control methods from a start to an end of imaging the object P in the radiation imaging system 100 according to the third embodiment disclosed herein.

In this imaging process, a threshold Dth of the dose (accumulated dose) and a change of the threshold Dth with the time are set based on the delay time Td and the reference value Dref of the dose (accumulated dose) obtained in advance, and the radiation imaging of the object P is performed.

Firstly, in step S601, the imaging condition setting unit 131 receives an instruction to start the imaging inputted by the operator via an input unit (not shown), and sets imaging condition information (irradiation condition information) inputted by the operator, for example. Here, the imaging condition setting unit 131 sets, as imaging condition information (irradiation condition information), a tube voltage and a tube current in the radiation tube 111, a reference value Dref of the dose (accumulated dose), a delay time Td, and the like. Thereafter, the imaging condition setting unit 131 transmits the acquired instruction for starting the imaging and the set imaging condition information (irradiation condition information) to the imaging control unit 133. The value of the delay time Td may be stored in any of the devices constituting the radiation imaging system 100, and the value may be referred to.

Subsequently, in step S602, the imaging control unit 133 sets the threshold Dth of the dose (accumulated dose) and its change with a time based on the reference value Dref of the dose (accumulated dose) and the delay time Td, set in step S601. The setting of the threshold Dth of dose (accumulated dose) and the change with the time will be described later with reference to FIG. 7.

Subsequently, in step S603, the imaging control unit 133 transmits an irradiation execution signal for irradiating the radiation R to the radiation generator 110 together with the imaging condition information (irradiation condition information) received from the imaging condition setting unit 131 in step S601. Accordingly, the radiation generator 110 irradiates the object P with radiation R under the irradiation conditions based on the imaging condition information (irradiation condition information) received from the imaging condition setting unit 131 and the threshold Dth set in step S602.

Subsequently, in step S604, the arithmetic unit 132 calculates a value D representing the dose (accumulated dose) of the radiation R detected by the sensor unit based on the dose information (for example, dose information for each of the imaging elements in the sensor unit) transmitted from the radiation imaging device 120. The value D representing the dose (accumulated dose) of the radiation R may be a maximum value, an average value, a median value or the like of the dose (accumulated dose). In the following description, the value D representing the dose (accumulated dose) of the radiation R is described as "dose (accumulated dose) D of the radiation R". Then, the imaging control unit 133 compares the dose (accumulated dose) D of the radiation R received from the arithmetic unit 132 with the threshold Dth set in step S602, and determines whether or not the dose (accumulated dose) D is smaller than the threshold Dth. As a result of this determination, if the dose (accumulated dose) D is smaller than the threshold Dth (step S604/YES), the process waits in step S604.

On the other hand, if it is determined in step S604 that the dose (accumulated dose) D is not smaller than the threshold Dth (dose (accumulated dose) D is equal to or larger than the threshold) (step S604/NO), the process proceeds to step S605. In step S605, since the dose (accumulated dose) D has exceeded (reached) the threshold Dth, the imaging control unit 133 outputs an irradiation stop signal for stopping the irradiation of the radiation R to the radiation generator 110. At this time, since the radiation R is continuously irradiated in a period of the delay time Td from the output of the irradiation stop signal from the imaging control unit 133 to the radiation generator 110 until the irradiation of the radiation R is actually stopped in the radiation generator 110, the dose (accumulated dose) D actually irradiated can be made closer to the reference value Dref of the dose (accumulated dose).

Subsequently, in step S606, the imaging control unit 133 firstly transmits an imaging control signal to the radiation imaging device 120. Then, the radiation imaging device 120 controls the imaging elements in the sensor unit based on the imaging control signal received from the imaging control unit 133, stops the conversion to the dose information after a predetermined time has elapsed from the reception of the imaging control signal, and transmits the generated radiation image data to the image processing unit 134.

Subsequently, in step S607, the image processing unit 134 performs the image processing such as a gradation processing and a noise reduction processing on the radiation image data received from the radiation imaging device 120. Thereafter, the image processing unit 134 transmits the radiation image data after the image processing to the display unit 135.

Subsequently, in step S608, the display unit 135 outputs a radiation image based on the radiation image data received from the image processing unit 134 to a monitor or the like for display, and presents the radiation image to the operator.

When the processing of step S608 is completed, the processing of the flowchart of the imaging of the object P shown in FIG. 6 is completed.

Next, with reference to FIG. 7, the process of setting the threshold Dth of the dose (accumulated dose) and the change with the time of the threshold Dth in step S602 of FIG. 6 will be described. When the change with the time of the threshold Dth of the dose (accumulated dose) is set, if an affirmative determination (step S604/YES) is made in step S604, the processing performed in step S602 is also performed.

Figure 7:
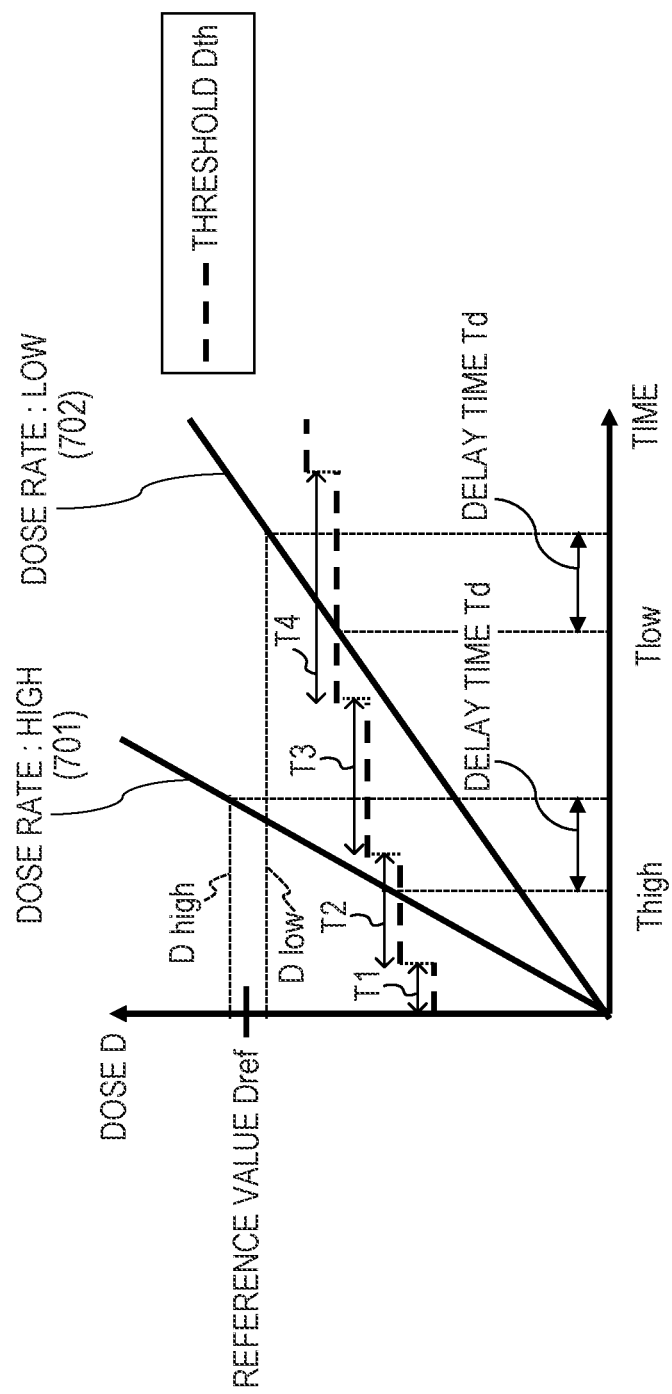
FIG. 7 is a diagram showing the third embodiment and an example of a threshold of a dose (accumulated dose) set in an imaging control unit and a relationship between a change of the threshold with the time and the dose (accumulated dose).

FIG. 7 shows an embodiment disclosed herein, and is a diagram showing an example of a threshold Dth of a dose (accumulated dose) set in the imaging control unit 133 and a relationship between a change of the threshold Dth with a time and a dose (accumulated dose) D. FIG. 7 shows the relationship between the dose (accumulated dose) D shown on the vertical axis and the time (elapsed time) shown on the horizontal axis.

As shown in FIG. 7, the imaging control unit 133 performs a control to change the threshold Dth of the dose (accumulated dose) in accordance with a elapsed time from a start of irradiation of the radiation R. Specifically, in FIG. 7, the imaging control unit 133 performs the control to increase the threshold Dth of the dose (accumulated dose) with the elapsed time.

When the dose (accumulated dose) D obtained from the arithmetic unit 132 is equal to or larger than the threshold Dth of the dose (accumulated dose) which changes in accordance with the elapsed time as shown in FIG. 7 (step S604/NO), the imaging control unit 133 outputs the irradiation stop signal to the radiation generator 110 in step S605 of FIG. 6. At this time, the radiation R is continuously irradiated by a period of the delay time Td from the output of the irradiation stop signal from the imaging control unit 133 to the radiation generator 110 until the irradiation of the radiation R is actually stopped in the radiation generator 110.

In the example shown in FIG. 7, when the dose rate 701 of the radiation R incident on the radiation imaging device 120 is high, the dose (accumulated dose) D obtained from the arithmetic unit 132 in the irradiation time Thigh is equal to or larger than the threshold Dth of the dose (accumulated dose). As a result, at the time of the irradiation time Thigh, the imaging control unit 133 outputs the irradiation stop signal to the radiation generator 110, and thereafter, the irradiation of the radiation R from the radiation generator 110 is stopped. In this case, the radiation R of the dose (accumulated dose) Dhigh reaches the radiation imaging device 120.

Similarly, in the case where the dose rate 702 of the radiation R incident on the radiation imaging device 120 is low, the dose (accumulated dose) D obtained from the arithmetic unit 132 in the irradiation time Tlow is equal to or greater than the threshold Dth of the dose (accumulated dose). As a result, at the time of the irradiation time Tlow, the imaging control unit 133 outputs the irradiation stop signal to the radiation generator 110, and thereafter, the irradiation of the radiation R from the radiation generator 110 is stopped. In this case, the radiation R of the dose (accumulated dose) Dlow reaches the radiation imaging device 120.

As shown in FIG. 7, the dose rate 701 and the dose rate 702 of the radiation R are determined based on the relationship between the dose (accumulated dose) D and the time. In FIG. 7, for example, when the threshold Dth of the dose (accumulated dose) is made constant, the actual dose (accumulated dose) D changes in accordance with the change in the dose rate, and becomes a value away from the reference value Dref of the dose (accumulated dose). On the other hand, in the present embodiment, as shown in FIG. 7, since a control is performed in which the threshold Dth of the dose (accumulated dose) is changed in accordance with the elapsed time from the start of irradiation of the radiation R (specifically, the threshold Dth of the dose (accumulated dose) is increased in accordance with the elapsed time.), both the dose (accumulated dose) Dhigh of the high dose rate 701 and the dose (accumulated dose) Dlow of the low dose rate 702 can be set to a value close to the reference value Dref of the dose (accumulated dose). Thus, the irradiation stop control of the radiation R can be performed with high accuracy regardless of the dose rate.

In this embodiment, as shown in FIG. 7, the change of the threshold Dth of the dose (accumulated dose) with the time can be expressed by a step function that changes stepwisely with respect to the elapsed time. In this case, the length of the time segments T1 to T4 of the step function relating to the threshold Dth of the dose (accumulated dose) may be different for each of the time segments as shown in FIG. 7. In this case, as shown in FIG. 7, if the lengths of the time segments T1 to T4 of the step function is gradually increased with the elapsed time (make T2 longer than T1, T3 longer than T2, T4 longer than T3), the number of time segments can be reduced. That is, in this case, the imaging control unit 133 decreases an increment amount per time of the threshold Dth of the dose (accumulated dose) with the elapsed time. If the number of time segments can be reduced, the memory to be used is reduced, and the load on the control unit 130 by changing the threshold Dth of the dose (accumulated dose) can be reduced.

In the present embodiment, the change of the threshold Dth of the dose (accumulated dose) with the time may be continuously changed with respect to the elapsed time.

In this embodiment, the threshold Dth of the dose (accumulated dose) with respect to the elapsed time t can be set to satisfy the following mathematic (1) by using the elapsed time t, the delay time Td, and the reference value Dref of the dose (accumulated dose).

$$Dth(t)=[t/(t+Td)]Dref \dots \quad (1)$$

That is, as shown in the mathematic (1), the imaging control unit 133 changes the threshold Dth of the dose (accumulated dose) in accordance with the elapsed time t, and sets the change of the threshold Dth of the dose (accumulated dose) with the time based the reference value Dref of the dose (accumulated dose) and the delay time Td.

When a step function is used as the threshold Dth of the dose (accumulated dose), it is desirable to set a function such that the mathematic (1) and each step of the steps intersect each other.

As described above, the imaging control unit 133 changes the threshold Dth of the dose (accumulated dose) in accordance with the elapsed time t, and sets the change of the threshold Dth of the dose (accumulated dose) with the time based on the reference value Dref of the dose (accumulated dose) and the delay time Td. According to this configuration, the irradiation stop control of the radiation from the radiation generator 110 can be performed with high accuracy. That is, the AEC can be performed with high accuracy.

That is, according to the disclosure of the present specification, the irradiation stop control of the radiation from the radiation generator can be performed with high accuracy.

The disclosure of this specification can also be realized by providing a program that implements one or more functions of the above embodiments to a system or device via a network or storage medium, with one or more processors in the computer of the system or device reading and executing the program. It can also be realized by a circuit (for example, ASIC) which realizes one or more functions. This program and a computer readable storage medium storing the program are included in the disclosure herein. The processor or circuit can also include a central processing unit (CPU), a microprocessing unit (MPU), a graphics processing unit (GPU), an application specific integrated circuit (ASIC), or a field programmable gateway (FPGA). The processor or circuit may also include a digital signal processor (DSP), a data flow processor (DFP), or a neural processing unit (NPU).

It should be noted that all of the above-described embodiments are merely examples of embodiments for carrying out the disclosure of this specification, and the technical scope of the disclosure of this specification should not be construed in a limited manner. That is, the disclosure of this specification can be implemented in various ways without departing from its technical philosophy or key features. Accordingly, in order to make the scope of the present invention public, the following claims are attached.

According to the disclosure of the present specification, it is possible to provide a mechanism capable of controlling the irradiation stop of the radiation from the radiation generator with high accuracy.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. A radiation imaging system comprising:
    a sensor unit configured to detect an incident radiation irradiated from a radiation generator; and
    one or more controllers configured to:
        acquire an accumulated dose of the radiation based on output of the sensor unit; and
        output a notification for stopping irradiation of the radiation in a case where the accumulated dose reaches or exceeds a threshold,
    wherein the one or more controllers set the threshold based on dose rate information corresponding to the radiation and delay time information, wherein the delay time information is information corresponding to a time from the outputting of the notification until the irradiation of the radiation by the radiation generator is stopped, and
    wherein the delay time information is acquired before the irradiation of the radiation.

2. The radiation imaging system according to claim 1, wherein the one or more controllers set a reference value of the accumulated dose before the irradiation of the radiation, and set the threshold by correcting the reference value based on the dose rate information and the delay time information.

3. The radiation imaging system according to claim 1, wherein the dose rate information of the radiation is acquired before the irradiation of the radiation, based on irradiation condition information including at least one of a tube voltage and a tube current of the radiation generator at a time of the irradiation of the radiation.

4. The radiation imaging system according to claim 1, wherein the dose rate information of the radiation is acquired before the irradiation of the radiation, based on radiation shield information including at least one of filter condition information at the time of the irradiation of the radiation in the radiation generating apparatus and object information to be irradiated with the radiation.

5. The radiation imaging system according to claim 1, wherein the dose rate information of the radiation, the delay time information, the amount of deviation between the reference value of the accumulated dose and the accumulated dose, and the object information are stored as imaging condition data and are used for subsequent radiation imaging.

6. A radiation imaging system comprising:
a sensor unit configured to detect an incident radiation irradiated from a radiation generator; and
one or more controllers configured to:
acquire an accumulated dose of the radiation based on output of the sensor unit; and
output a notification for stopping irradiation of the radiation in a case where the accumulated dose satisfies a threshold condition,
wherein the threshold condition is a condition for reducing deviation caused by radiation irradiation stop timing affected by communication delay with the radiation generator,
wherein the threshold condition comprises at least a first threshold value and a second threshold value larger than the first threshold value,
wherein the first threshold value is a threshold value used in a first timing, and the second threshold value is a threshold value used in a second timing in which the elapsed time from the irradiation start timing of the radiation is longer than that of the first timing.

7. The radiation imaging system according to claim 6, wherein one or more controllers are configured to increase the threshold with the elapsed time.

8. The radiation imaging system according to claim 6, wherein the one or more controllers decrease an increment amount of the threshold per a unit time, with the elapsed time.

9. The radiation imaging system according to claim 6, wherein the delay time information is acquired before the irradiation of the radiation for each imaging environment.

10. The radiation imaging system according to claim 6 wherein the delay time information is determined by taking into account an unsteady period of the radiation generator.

11. The radiation imaging system according to claim 6, wherein a change of the threshold is represented by a step function that changes step-wise with respect to the elapsed time.

12. The radiation imaging system according to claim 11, wherein a length of a time segment in the step function varies for each of the time segments.

13. The radiation imaging system according to claim 11, wherein a length of a time segment in the step function gradually increases with the elapsed time.

14. The radiation imaging system according to claim 6, wherein the change of the threshold varies continuously with the elapsed time.

15. The radiation imaging system according to claim 6, wherein when the elapsed time is expressed by t, the delay time information is expressed by Td, the reference value of the dose is expressed by Dref, and the threshold for the elapsed time is expressed by Dth(t), the following expression (1) is satisfied $$Dth(t)=[t/(t+Td)]Dref \ldots \quad (1).$$

16. The radiation imaging system according to claim 1, further comprising the radiation generator.

17. A control apparatus configured to be capable of communicating with a radiation imaging apparatus comprising a sensor unit for detecting an incident radiation irradiated from a radiation generator, the control apparatus comprising:
one or more controllers configured to:
acquire an accumulated dose of the radiation based on output of the sensor unit; and
output a notification for stopping irradiation of the radiation in a case where the accumulated dose reaches or exceeds a threshold,
wherein the one or more controllers set the threshold based on dose rate information corresponding to the radiation and delay time information, wherein the delay time information is information corresponding to a time from outputting of the notification until the irradiation of the radiation by the radiation generator is stopped, and
wherein the delay time information is acquired before the irradiation of the radiation.

18. A method for controlling a radiation imaging system comprising a sensor unit for detecting an incident radiation irradiated from a radiation generator, comprising:
an acquisition step of acquiring an accumulated dose of the radiation based on output of the sensor unit;
a setting step of setting a threshold; and
an output step of outputting a notification for stopping irradiation of the radiation in a cae where the accumulated dose reaches or exceeds a threshold,
wherein in the setting step, the threshold is set based on dose rate information corresponding to the radiation and delay time information, wherein the delay time information is information corresponding to a time from the outputting of the notification until the irradiation of the radiation by the radiation generator is stopped, and
wherein the delay time information is acquired before the irradiation of the radiation.

19. A control apparatus configured to be capable of communicating with a radiation imaging apparatus comprising a sensor unit for detecting an incident radiation irradiated from a radiation generator, the control apparatus comprising:
one or more controllers configured to:
acquire an accumulated dose of the radiation based on output of the sensor unit; and
output a notification for stopping irradiation of the radiation in a case where the accumulated dose satisfies a threshold condition,
wherein the threshold condition is a condition for reducing deviation caused by radiation irradiation stop timing affected by communication delay with the radiation generator,
wherein the threshold condition comprises at least a first threshold value and a second threshold value larger than the first threshold value,
wherein the first threshold value is a threshold value used in a first timing, and the second threshold value is a threshold value used in a second timing in which the elapsed time from the irradiation start timing of the radiation is longer than that of the first timing.

20. A method for controlling a radiographic system comprising a sensor unit for detecting incident radiation irradiated from a radiation generator, comprising:
an acquisition step of acquiring an accumulated dose of the radiation based on output of the sensor unit; and an output step of outputting a notification for stopping irradiation of the radiation in a case where the accumulated dose is satisfies a threshold condition,
wherein threshold condition is a condition for reducing deviation caused by radiation irradiation stop timing affected by communication delay with the radiation generator,
wherein the threshold condition comprises at least a first threshold value and a second threshold value larger than the first threshold value,
wherein the first threshold value is a threshold value used in a first timing, and the second threshold value is a threshold value used in a second timing in which the elapsed time from the irradiation start timing of the radiation is longer than that of the first timing.

* * * * *